US012642806B2

(12) United States Patent
Bolton et al.

(10) Patent No.: US 12,642,806 B2
(45) Date of Patent: Jun. 2, 2026

(54) CANNABIDIOL COMPOSITIONS FOR USE IN TREATING HEART CONDITIONS

(71) Applicant: CARDIOL THERAPEUTICS INC., Oakville (CA)

(72) Inventors: Anthony Ernest Bolton, Oakville (CA); Blagoja Ristevski, Oakville (CA); Guillermo Torre Amione, Real de San Agustin (MX); Gerardo De Jesús García Rivas, Monterrey (MX); Omar Lozano García, Monterrey (MX); Eldon Raymond Smith, Calgary (CA)

(73) Assignee: Cardiol Therapeutics Inc., Oakville (CA)

( * ) Notice: Subject to any disclaimer, the term of this patent is extended or adjusted under 35 U.S.C. 154(b) by 1078 days.

(21) Appl. No.: 17/755,127

(22) PCT Filed: Oct. 20, 2020

(86) PCT No.: PCT/CA2020/051405

§ 371 (c)(1),
(2) Date: Apr. 21, 2022

(87) PCT Pub. No.: WO2021/077211

PCT Pub. Date: Apr. 29, 2021

(65) Prior Publication Data

US 2022/0401380 A1 Dec. 22, 2022

Related U.S. Application Data

(60) Provisional application No. 62/926,066, filed on Oct. 25, 2019.

(51) Int. Cl.

| | |
|---|---|
| ***A61K 31/05*** | (2006.01) |
| ***A61K 9/00*** | (2006.01) |
| ***A61K 31/00*** | (2006.01) |
| ***A61K 36/185*** | (2006.01) |
| ***A61K 47/14*** | (2017.01) |
| ***A61P 9/10*** | (2006.01) |

(52) U.S. Cl.

CPC .......... *A61K 31/658* (2023.05); *A61K 9/0019* (2013.01); *A61K 36/3482* (2024.05); *A61K 47/14* (2013.01); *A61P 9/10* (2018.01)

(58) Field of Classification Search

CPC ...................................................... A61K 31/05
See application file for complete search history.

(56) References Cited

U.S. PATENT DOCUMENTS

| | | | |
|---|---|---|---|
| 2013/0245110 | A1 | 9/2013 | Guy et al. |
| 2016/0008305 | A1 | 1/2016 | Rubinstein et al. |
| 2017/0049830 | A1 | 2/2017 | Raderman |

FOREIGN PATENT DOCUMENTS

| | | | |
|---|---|---|---|
| CN | 108126012 | A | 6/2018 |
| WO | 2003/063847 | A1 | 8/2003 |
| WO | 2014/160153 | A1 | 10/2014 |
| WO | 2016/103254 | A1 | 6/2016 |
| WO | 2017/054071 | A1 | 4/2017 |
| WO | 2018061007 | A1 | 4/2018 |
| WO | 2018/096504 | A1 | 5/2018 |
| WO | 2019/014851 | A1 | 1/2019 |
| WO | 2019/113685 | A1 | 6/2019 |
| WO | WO 2019113685 | * | 6/2019 |
| WO | 2019135225 | A1 | 7/2019 |

OTHER PUBLICATIONS

Prakash Nagarkatti et al., Cannabinoids as novel anti-inflammatory drugs, Future Med Chem. Oct. 2009 ; 1(7):1333-1349. doi:10.4155/fmc.09.93.

Office Action issued with corresponding Israeli Patent Application No. 291936 dated Jan. 1, 2025.

Lee et al., "Cannabidiol Limits T Cell-Mediated Chronic Autoimmune Myocarditis: Implications to Autoimmune Disorders and Organ Transplantation", Molecular Medicine, vol. 22, 2016, pp. 136-146.

Office Action issued with corresponding Japanese Patent Application No. 2022-521100 dated Sep. 26, 2024 (including English Translation).

Rajesh et al., Cannabidiol attenuates cardiac dysfunction, oxidative stress, fibrosis, and inflammatory and cell death signaling pathways in diabetic cardiomyopathy. Journal of the American College of Cardiology (2010) vol. 56(25), pp. 2115-2125.

Hao et al., Cannabidiol Protects against Doxorubicin-Induced Cardiomyopathy by Modulating Mitochondrial Function and Biogenesis. Mol. Med.(2015) vol. 21(1), pp. 38-45.

Gollmer et al., Established and Emerging Mechanisms of Diabetic Cardiomyopathy. Lipid Atheroscler. (2019) vol. 8 (1), pp. 26-47.

Al-Taee et al., β-caryophyllene, a dietary phytocannabinoid attenuates oxidative stress, inflammation, apoptosis and prevents structural alterations of the myocardium against doxorubicin-induced acute cardiotoxicity in rats: An in vitro and in vivo study. European Journal of Pharmacology (2019) vol. 858, pp. 1-10.

* cited by examiner

*Primary Examiner* — Rei Tsang Shiao
(74) *Attorney, Agent, or Firm* — Troutman Pepper Locke LLP

(57) ABSTRACT

A pharmaceutical composition containing an effective amount of cannabidiol (CBD) for use in treating or preventing a heart condition, along with related methods and uses. The heart conditions include heart failure, acute myocarditis, toxicity caused by anti-cancer therapies, acute pericarditis, cardiac sarcoidosis, inflammatory cardiomyopathy, and atherosclerosis and related uses and methods. The disclosure shows CBD to be effective in (i) reducing cardiac hypertrophy; (ii) reducing cardiac fibrosis; (iii) reducing the level of BNP; (iv) reducing the level of cytokine IL1β; (v) reducing the level of cytokine IL6; (vi) reducing the level of CD69; (vii) increasing the level of cytokine IL10, and (viii) combinations thereof. The composition is preferably adapted for parenteral administration.

20 Claims, 17 Drawing Sheets

*** = p<0.001 vs CTRL
### = p<0.001 vs ANG

* = p<0.05 vs CTRL
** = p<0.01 vs CTRL
# = p<0.05 vs ANG
## = p<0.01 vs ANG

* = p<0.05 vs CTRL
# = p<0.05 vs ANG

# = p<0.05 vs ANG

Heart Failure Protocol

HF

ATII

L-NAME/NaCl

HF + formulation

ATII

L-NAME/NaCl

Formulation administration at selected dose, frequency, and route of administration 5 weeks: 1 week L-NAME/NaCl, 4 weeks Angiotensin II Analysis upon upper and lower parts of the heart:
Fibrosis and myocyte size;
Cardiac remodelling and inflammatory markers.

*** = p<0.001 vs CTRL
### = p<0.001 vs ANG

*** = p<0.001 vs CTRL
### = p<0.001 vs ANG

*** = p<0.001 vs CTRL
# = p<0.05 vs ANG
### = p<0.001 vs ANG

*** = p<0.001 vs CTRL
# = p<0.05 vs ANG
## = p<0.01 vs ANG

## = p<0.01 vs ANG

CANNABIDIOL COMPOSITIONS FOR USE IN TREATING HEART CONDITIONS

CROSS-REFERENCE TO RELATED APPLICATIONS

This application is a § 371 National Phase Application of PCT Application Serial No. PCT/CA2020/051405 filed on Oct. 20, 2020 entitled "Cannabidiol Compositions for Use in Treating Heart Conditions," which claims priority to U.S. Provisional Patent Application 62/926,066 filed Oct. 25, 2019 entitled "Parenteral Cannabidiol Compositions for Treating Heart Conditions," the entire contents of all of the applications identified above are incorporated herein by reference.

FIELD

The present invention relates generally to pharmaceutical compositions containing cannabidiol (CBD) as well as to the treatment or prevention of diseases and disorders using such compositions.

BACKGROUND

Chronic Heart Failure (CHF) affects more than 26 million people globally. Over six million adults in Canada and the United States suffer from chronic heart failure and it remains a leading cause of death and hospitalization, with associated healthcare costs exceeding $30 billion annually in the U.S. alone.

People with heart failure (HF) suffer from shortness of breath, rapid heart rate, edema, and reduced exercise capacity. They often struggle with simple daily activities and are frequently hospitalized. For many, these symptoms significantly reduce quality of life.

Heart failure occurs when the heart is no longer able to pump blood sufficient for the body's needs. There are two types of heart failure: heart failure with reduced ejection fraction (HFrEF, referred to also as systolic heart failure) and heart failure with preserved ejection fraction (HFpEF, formerly referred to as diastolic heart failure). In heart failure with reduced ejection fraction (HFrEF), there is a reduced contraction of the left ventricle such that not enough blood is pumped into the circulation with each contraction of the heart. In heart failure with preserved ejection fraction (HFpEF), the problem is primarily in restriction to filling of the left ventricle during the relaxation period. The pathology results in the left ventricle becoming stiff and it does not relax normally. As a result, it cannot fill properly and pressure begins to increase in the left heart chambers and in the lungs. The increased pressure in the lungs is the cause of shortness of breath.

HFpEF is a complex syndrome. The pathophysiological mechanisms are still not totally understood, which is one reason why there is no effective treatment to date. However, it has been noted that a number of conditions are frequently associated with HFpEF. Important among these is components of the metabolic syndrome (glucose intolerance, obesity, hypertension and lipid abnormalities). Of particular importance is obesity which creates a generalized inflammatory state and contributes to heart inflammation which, in turn, is associated with fibrosis and reduced ventricular compliance (relaxation). Hypertension (HTN) is also a major precursor condition to HFpEF and leads to increased left ventricular (LV) muscle thickness (LV hypertrophy) and also reduced LV compliance. This inability of the left ventricle to fill properly is also referred to as left ventricular diastolic dysfunction (LVDD). HTN is considered by some to be the most significant risk factor for the development of LVDD.

The publication, Glezeva et al., "Role of inflammation in the pathogenesis of heart failure with preserved ejection fraction and its potential as a therapeutic target," (Heart Fail Rev (2014) 19:681-694; DOI 10.1007/s10741-013-9405-8), incorporated herein by reference, describes studies showing that inflammation is an initial and primary trigger of ventricular remodelling in HTN, contributing to LVDD. The studies suggest that inflammation is caused by elevated levels of endothelial adhesion molecules as well as increased production and release of inflammatory cytokines and chemokines in the tissue. The latter promotes the infiltration of activated inflammatory cells, particularly monocytes, into the cardiac tissue. Increased monocyte infiltration is seen in the early and late stages of HTN and HFpEF. Once inside the tissue, monocytes are believed to differentiate into macrophages and promote cardiac inflammation, tissue injury, and myocardial fibrosis. This mechanism is believed to be part of the progression towards HFpEF. The authors concluded that myocardial inflammation has an important role in HFpEF pathophysiology and propose that therapeutic approaches intervening in the inflammatory pathway should be utilized in addition to an anti-hypertensive treatment in at-risk patients or patients with LVDD and/or HFpEF. They conclude that more large randomised clinical trials in patients with HFpEF along with a better understanding of the ongoing inflammatory reactions in HTN and LVDD are needed.

In addition to hypertension, there are several risk factors associated with the development of HFpEF. The first is diabetes mellitus, which is a common risk factor for, not only heart failure, but atherosclerosis of the coronary arteries, the usual cause of heart attacks. The other major risk factors are obesity and ageing. Interestingly, ageing, diabetes and obesity are all conditions associated with increased systemic inflammation. Fat cells are major producers of inflammatory cytokines which circulate to other tissues. The combination of hypertension, diabetes and obesity is extremely common in HFpEF and each contributes to the inflammatory milieu which many believe to be the cause of this syndrome.

Cannabinoids are compounds found naturally in the plant *Cannabis sativa*. The major cannabinoid constituents include cannabidiol (CBD) and tetrahydrocannabinol (THC). THC is known to increase pulse rate, cause conjunctival reddening, and provide psychotropic (mood altering) effects such as a feeling of euphoria. CBD is non-intoxicating in contrast to THC. Thus, CBD is more commonly used as a medicinal ingredient for treating a wide range of conditions including epilepsy, chronic pain, anxiety, and insomnia. The anti-inflammatory effects of CBD have been mentioned in a number of publications. See, e.g., WO 2014/117999 A1 (chronic inflammation and inflammatory diseases), WO 2017/191630 A1 (liver inflammation), U.S. Pat. No. 9,549,906 (ocular inflammation) and WO2018148152 (neuroinflammation).

Cannabidiol (CBD) is lipid soluble and virtually insoluble in water. Furthermore, it is sensitive to deactivation in the liver via first-pass metabolism. This high first-pass metabolism results in low active blood levels and overall bioavailability of less than 10% when taken orally.

There is an ongoing need to provide improved compositions containing CBD that avoid first-pass hepatic metabolism to optimize and maintain blood levels of the drug. There is also an ongoing need to better understand the pathophysiological mechanisms of heart conditions, including heart failure, and to provide new therapies to treat and/or prevent same.

SUMMARY

The inventors have found that CBD administered parenterally, e.g. subcutaneously, is effective to reduce cardiac hypertrophy and myocardial fibrosis, as well as to beneficially modulate the level of molecular markers of remodeling and inflammation in an in vivo non-ischemic (hypertension-induced) murine model of heart failure. Surprisingly, these effects were observed at very low doses. The inventors have also found that CBD is effective to prevent cell enlargement (hypertrophy) in a model of cardiomyocyte hypertrophy using H9c2 cells in vitro. Furthermore, the inventors have conducted a study showing that CBD is effective to reduce the expression of CD69 (a marker of inflammation), by human lymphocytes and monocytes in vitro. These findings, as well as findings in the published literature, support the beneficial role of CBD in treating or preventing heart conditions, including heart failure (e.g. HFpEF), acute myocarditis, toxicity caused by certain anti-cancer therapies (e.g. doxorubicin, checkpoint inhibitors), acute pericarditis, cardiac sarcoidosis, certain dilated cardiomyopathies (inflammatory cardiomyopathy) and even atherosclerosis (coronary artery disease). These heart conditions each has inflammation as a prominent component and involve variable degrees of hypertrophy or fibrosis.

Therefore, according to a first aspect, the present invention provides the use of an effective amount of CBD to treat or prevent a heart condition selected from the group consisting of heart failure (e.g. HFpEF), acute myocarditis, toxicity caused by anti-cancer therapies (e.g. doxorubicin, checkpoint inhibitors), acute pericarditis, cardiac sarcoidosis, inflammatory cardiomyopathy, and atherosclerosis.

In certain embodiments, the use of CBD is effective to:

(a) reduce cardiac hypertrophy;
(b) reduce cardiac fibrosis;
(c) reduce the level of BNP;
(d) reduce the level of cytokine IL1β;
(e) reduce the level of IL6;
(f) reduce the level of CD69;
(g) increase the level of cytokine IL10; or
(h) effect any combination of the above;
in the subject.

In selected embodiments, the CBD is used to effect at least 2, 3, 4, 5, 6, or all of (a) to (g) above in the subject.

The skilled person will appreciate that cardiac function, including cardiac dilatation, in heart failure subjects is improved when a reduction in blood level of BNP is observed. Furthermore, when the levels of cytokines IL1β, IL6 and CD69 are reduced, or the level of cytokine IL10 is increased, this indicates reduced inflammation which is known to underlie the inflammatory heart conditions mentioned above.

The CBD can be present in a parenteral composition according to a second aspect of the invention, the composition comprising, consisting essentially of, or consisting of an effective amount of CBD and an effective amount of at least one pharmaceutically acceptable solvent for solubilizing the CBD in the composition. Administering CBD parenterally will avoid first-pass hepatic metabolism and therefore optimize and maintain blood levels of the drug. The present compositions are adapted to be administered via any parenteral route, including via intramuscular (IM), intravenous (IV), intraperitoneal (IP), and subcutaneous (SC) routes of injection. Preferably, the compositions are adapted to be administered via SC and IM injection.

The present invention also contemplates using CBD in combination with one or more additional anti-inflammatory pharmaceutically active agents, such as beta-caryophyllene (BCP), methotrexate (MTX), and cyclosporine (CsA). These other agents can be administered with CBD contemporaneously or sequentially, and (depending on the agent) may be administered with CBD in the same composition. BCP and CsA are agents that can be included in the same composition as CBD. In some embodiments, the pharmaceutically active agent in the composition consists of CBD. In other embodiments, the pharmaceutically active agent consists of CBD and BCP. Furthermore, the present uses, compositions and methods can be an adjunct to existing therapeutics and methods for treating heart conditions to improve patient outcomes.

The at least one pharmaceutically acceptable solvent can be selected from the group consisting of natural and synthetic medium chain (C6-C12) triglycerides (MCTs), structured lipids, propylene glycol dicaprylate/dicaprate, vegetable oils, N-methyl-2-pyrrolidone, polyoxyethylene castor oil derivatives, dimethylacetamide (DMA), ethanol, glycerin, PEG 300, PEG 400, polyoxyethylene 20 sorbitan monooleate, propylene glycol (PG), polyglycol mono- and diesters of 12-hydroxystearic acid, solvents sold in association with the trademark Kolliphor™, and mixtures thereof. These solvents are useful for solubilizing lipophilic compounds such as CBD, BCP, and CsA. On the other hand, other (hydrophilic) solvents would be used for MTX which is not lipophilic.

In some embodiments, the at least one pharmaceutically acceptable solvent is selected from the group consisting of natural and synthetic medium chain (C6-C12) triglycerides (MCTs). Furthermore, at least about 95% of the MCTs can consist of a C8 triglyceride, a C10 triglyceride, or a mixture thereof.

The pharmaceutically active agent is present in an "effective amount" defined hereinbelow. In embodiments wherein the pharmaceutically active agent consists of CBD, or CBD and BCP, the pharmaceutically active agent can each be present in an amount of at least about 10, 20, 30, 40, 50, 60, 70, 80, 90, or 100 mg/mL of the composition. Alternatively or additionally, the pharmaceutically active agent can each be present in an amount up to about 350, 300, 250, 200, or 150 mg/mL of the composition. Typically, from about 0.1, 0.5, 1, 1.5, 2, 3, or 4 and up to about 30, 25, 20, 15, 10, 9, 8, 7, 6, or 5 mg of each pharmaceutically active agent is administered per kg body weight. Preferably, each pharmaceutically active agent is administered in an amount from about 0.1 to about 10 mg/kg body weight, or from about 1 to about 10 mg/kg body weight.

In embodiments wherein the pharmaceutically active agent consists of CBD and BCP, the weight ratio of CBD to BCP can vary provided that each active is present in an effective amount. For example, the weight ratio of CBD to BCP can be from about 1:4 to about 4:1, from about 1:2 to about 2:1, or about 1:1.

In some embodiments, the parenteral composition is substantially free of water. In the same or other embodiments, the composition is substantially free of micelles.

According to a third aspect, the invention provides a method of treating and/or preventing a heart condition selected from the group consisting of heart failure (e.g. HFpEF), acute myocarditis, toxicity caused by anti-cancer therapies (e.g. doxorubicin, checkpoint inhibitors), acute pericarditis, cardiac sarcoidosis, inflammatory cardiomyopathy, and atherosclerosis. The method comprises:

(i) identifying a subject having, or at risk of having, said heart condition; and (ii) administering an effective amount of CBD to the subject;

wherein the administration of CBD:

(a) reduces cardiac hypertrophy;

(b) reduces cardiac fibrosis;

(c) reduces the level of BNP;

(d) reduces the level of cytokine IL1β;

(e) reduces the level of IL6;

(f) reduces the level of CD69;

(g) increases the level of cytokine IL10; or effects any combination of the above;

in the subject.

In selected embodiments, the administration of CBD effects at least 2, 3, 4, 5, 6, or all of (a) to (g) above in the subject.

Preferably, the administration is via a parenteral route to avoid first-pass hepatic metabolism. Therefore, the CBD can be present in a parenteral composition according to the second aspect of the invention.

In methods according to the invention, the composition can be administered at least 1, 2 or 3 times weekly, at least once daily, or at least twice daily, for a period of 1, 2, 3, 4, 5, 6, 7, 8, or more weeks. When treating a chronic condition, it is envisioned that the treatment period may be for an indefinite length of time and the amount of the pharmaceutically active ingredient is adjusted to a dose so as to avoid long term toxicity. Depending on the frequency of administration, each dose of the parenteral composition can contain from about 1, 2, 3, 4, or 5 and up to about 20, 15, or 10 mg CBD (or each of CBD and BCP) per kg body weight.

Subjects at risk of developing heart failure (HFpEF) are those who are older in age (e.g. 60 years or age or older), as well as those who have hypertension, diabetes, and/or obesity. As for acute myocarditis, this is a post-viral condition and the demographic affected can be young individuals. Cardiac sarcoidosis is uncommon overall but is seen more in African-Americans and usually in the age group of 30 to 40 years. It is characterized by the presence of granulomas within the cardiac tissue which may require endo-myocardial biopsy for diagnosis. Inflammatory cardiomyopathy often occurs in younger adults and leads to chronic heart failure. In some cases it may be the end-result of acute myocarditis. Increasingly patients with cancer are receiving drugs (such as anthracyclines and Check-point Inhibitors) which can impact the heart, leading to an inflammation-induced damage. In some cases, for example, after receiving checkpoint inhibitors, the condition can rapidly deteriorate and result in cardiogenic shock or death. Acute pericarditis is an acute inflammation of the pericardial sac which can involve variable inflammatory damage to the adjacent heart. It also tends to occur in a young population although it can occur at any age. Atherosclerotic heart disease is the common cause of myocardial infarction which is usually associated with thrombosis of a coronary artery. The pathogenesis of the thrombus is widely believed to result, at least in part, from an inflammatory process in the artery wall.

BRIEF DESCRIPTION OF FIGURES

The invention may be better understood with reference to the following description taken together with the following drawings in which.

Figure 1:
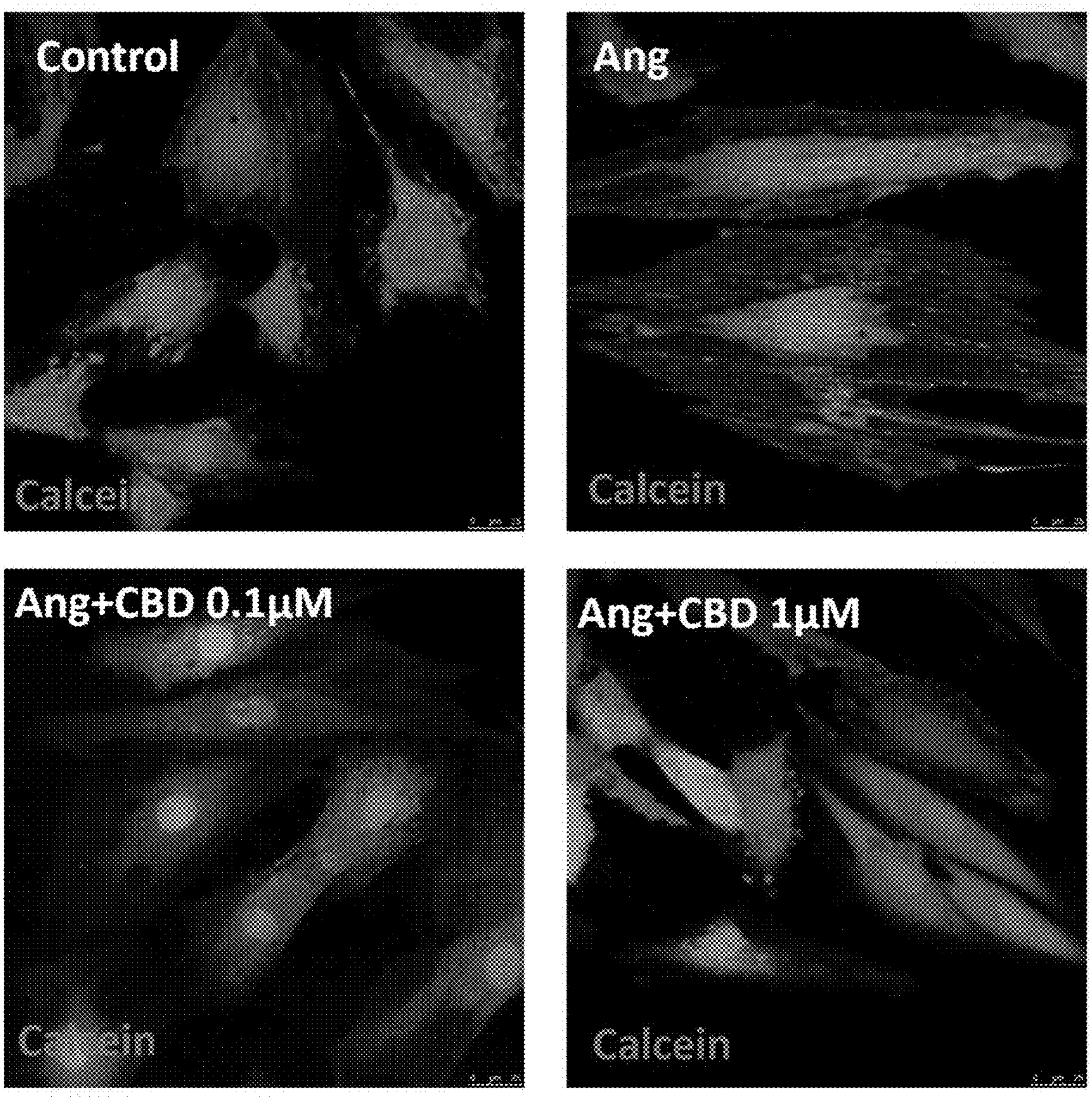
FIG. 1 contains selected confocal microscopy images showing the effect of administration of CBD at different doses on the cell surface area of H9c2 cells, in an in vitro model of cardiomyocyte hypertrophy.

In the figures, "p values" are indicated as * or #=≤0.05,  or ##=≤0.01, and * or ###=≤0.001. The lower the "p value", the greater the significance between groups.

DETAILED DESCRIPTION

Definitions

For the sake of clarity and to avoid ambiguity, certain terms are defined herein as follows.

The term "pharmaceutically active agent" means any composition of matter (e.g. agent, compound, or ingredient) capable of providing a therapeutic effect (e.g. healing, alleviating, preventing a disease or its symptoms) to a subject, including drugs, cells, DNA, RNA, oligonucleotides, proteins, and peptides.

When a composition of matter, e.g. a compound or ingredient, is described as having a "purity of X %" this means that one or more impurities may be present in an amount up to 100-X % by weight, based on the total weight of the composition of matter. The purity of an ingredient can be determined by high performance liquid chromatography (HPLC) or other suitable means.

The term "subject" means members of the animal kingdom including humans and other mammals.

When used herein, the term "treatment" is intended to mean stopping or delaying the progression of a condition, disorder or disease. The term "prevention" means preventing or delaying the onset of a condition, disorder or disease. The terms are intended to encompass "improving quality of life," "extending the life," and "improving clinical outcomes" of a subject suffering from, or at risk of suffering from, the condition, disorder or disease, and do not necessarily mean "curing" the condition, disorder or disease.

"Pharmaceutically acceptable excipient" when used herein means any substance which can be formulated with or that is present alongside a pharmaceutically active agent to achieve a desired function or functions. To be "pharmaceutically acceptable", the excipient must be non-toxic, safe to humans and animals, and compatible with the other ingredients in the composition, having regard to the parenteral mode of administration. The person skilled in the art will appreciate what compounds or ingredients would qualify as a pharmaceutically acceptable excipient given the teachings of the present specification and information in the public domain.

"Pharmaceutically acceptable solvent" means a pharmaceutically acceptable excipient that is effective (whether taken alone or in combination with other pharmaceutically acceptable excipients) to solubilize at least one pharmaceutically active agent in the overall composition.

The phrases "at least one," "one or more," and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The terms "a" or "an" entity refers to one or more of that entity. As such, the terms "a" (or "an"), "one or more" and "at least one" can be used interchangeably herein. It should also be noted that the term "or" is generally employed in the sense of "and/or" unless the context clearly dictates otherwise.

The term "comprising" means "including without limitation." Thus, a composition comprising a list of ingredients may include additional ingredients not expressly recited. It is also to be noted that the terms "comprising," "including," and "having" can be used interchangeably.

The term "consisting of" means "including the listed ingredients and such additional ingredients as may be present in the listed ingredients as natural or commercial impurities or additives." Natural and commercial impurities and additives will be apparent to the person of ordinary skill in the art. Synthetic cannabidiol (CBD) may contain up to about 0.5% w/w of impurities such as residual solvents and by-products of the manufacturing process. Therefore, a composition "consisting of synthetic CBD" means that the composition has at least about 99.5 w/w of CBD and up to about 0.5 wt. % impurities.

The term "consisting essentially of" means "including the listed ingredients and any additional ingredients that do not materially affect the basic and novel properties of the invention." By "basic and novel properties" is meant the utility of the present compositions in treating or preventing the heart conditions specified herein. In embodiments in which CBD is employed, "basic and novel properties" also means the stability and solubility of the CBD in the composition and suitability of the composition for parenteral administration.

Unless stated otherwise, the term "weight percent," "% w/w," "percent by weight," "% by weight," "wt. %," and variations thereof, refer to the amount of a substance as the weight of that substance divided by the total weight of the composition containing that substance, and multiplied by 100.

Unless stated otherwise, the term "volume percent," "vol. %," "percent by volume," "% by volume," % v/v, and variations thereof, refer to the amount of a substance as the volume of that substance divided by the total volume of the composition containing that substance, and multiplied by 100.

The term "about" refers to variations in an expressed numerical quantity that can occur, for example, through measuring and liquid handling procedures used for making pharmaceutical compositions, differences in the manufacture, source, or purity of the ingredients used to make the compositions, and/or differences due to different equilibrium conditions or different reaction levels of ingredients in a composition resulting from an initial mixture. For the sake of clarity, the term "about" includes variations in the expressed value up to ±5%. Whether or not a value is modified by the term "about," the claims include equivalents to the values.

When used herein, the term "effective amount" means an amount that would bring about the desired effect, based on the known purpose and function of the ingredient in the context of the invention. For example, an effective amount of a pharmaceutically active agent is that amount which would be effective to provide a therapeutic effect as described herein. An effective amount of a solvent is that amount which, alone or together with other ingredients, would be effective to solubilize the other or remaining ingredients of the composition. What constitutes an effective amount will be determinable by the person of ordinary skill in the art by routine experimentation, having regard to the teachings herein.

When used herein, the expression "substantially free of Y" means that "Y" is not deliberately added but may be present as an impurity or due to other factors. For example, in the case of parenteral compositions that are substantially free of water, the composition may contain minute amounts of water due to water being present in the atmosphere and the composition or ingredients thereof being exposed to the atmosphere. For the sake of clarity, a composition that is "substantially free of Y" will not contain Y or only up to 0.5% w/w of "Y," based on the composition.

The values recited herein are intended to include all values that meet the stated parameters including those not expressly recited. Thus, for example, a value of less than 1.0% w/w is intended to include less than 0.99% w/w, less than 0.98 wt. %, less than 0.97 wt. %, less than 0.90% w/w, less than 0.84% w/w, less than 0.56% w/w, less than 0.01% w/w, etc. Thus, all ranges disclosed herein are to be understood to encompass any and all subranges subsumed therein. For example, a stated range of "1 to 10" should be considered to include any and all subranges between (and inclusive of) the minimum value of 1 and the maximum value of 10, e.g., 1 to 6.3, or 5.5 to 10, or 2.7 to 6.1, etc.

The present specification contemplates the possibility of omitting any components even if they are not expressly named as included or excluded in the specification.

The chemical structures herein are drawn according to the conventional standards known in the art. Thus, where an atom, such as a carbon atom, as drawn appears to have an unsatisfied valency, then that valency is assumed to be satisfied by a hydrogen atom, even though that hydrogen atom is not necessarily explicitly drawn. The structures of some of the compounds of this specification include stereogenic carbon atoms. That is, any chiral carbon center may be of either (R)- or (S)-stereochemistry. It is to be understood that isomers arising from such asymmetry (e.g., all enantiomers and diastereomers) are included within the scope of this specification to the extent that such isomers are known to have pharmaceutical activity, as would be understood by the person skilled in the art. Such isomers can be obtained in substantially pure form by classical separation techniques and by stereochemically-controlled synthesis. Furthermore, alkenes can include either the E- or Z-geometry, where appropriate. The geometry applicable is that which would provide the desired pharmaceutical activity.

Cannabidiol (CBD)

The present compositions contain (at least) cannabidiol (CBD) as the pharmaceutically active agent. The terms cannabidiol and CBD are used interchangeably herein and refer to the compound having the below chemical structure:

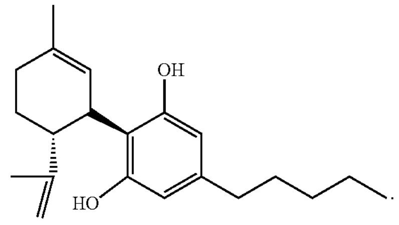

CBD

The CBD can be of natural or synthetic origin, and in crystalline or oil form. All commercial sources of CBD are useful in the context of the present invention.

Preferably, the CBD has a purity of at least 99.5%, 99.6%, 99.7%, 99.8% or 99.9%.

"Synthetic cannabinoids" are compounds that have a cannabinoid-like structure and are manufactured using chemical or biosynthetic means. Methods of manufacturing synthetic cannabidiol are known in the art. For example, the CBD from NORAIVICO, INC. headquartered in Wilmington Delaware, U.S.A. is made according to processes such as those described in U.S. patent publication US 2017/0008868 A1 (granted as U.S. Pat. No. 10,059,683) and US 2018/031,976 A1, incorporated herein by reference. Synthetic CBD made by other processes and manufacturers can also be used to make the present compositions provided they have the desired level of purity.

Botanically sourced CBD can be derived from a variety of cannabis plants, including hemp, and purified using conventional means.

The terms tetrahydrocannabinol, THC, delta-9-tetrahydrocannabinol, and delta-9-THC are used interchangeably herein and refer to the chemical compound having the structure shown hereinbelow. The term is used broadly herein to include the double bond isomers and their stereoisomers.

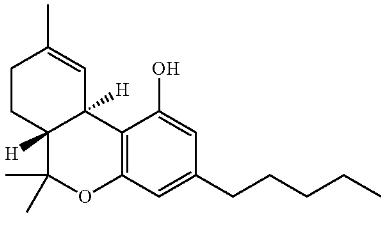

THC

The skilled person will appreciate that commercial sources of CBD may contain minor amounts of impurities, including THC. For example, synthetic CBD may contain small amounts of residual solvents (e.g. methanol, n-heptane, dichloromethane, and triethylamine) and by-products of manufacture, e.g. olivetol, monobromo-CBD, and delta-9-THC. Botanically sourced CBD may contain small amounts of other cannabinoids (including THC), terpenes, and solvents or ingredients used in the purification process.

In some embodiments, the present compositions are "substantially free" of THC, meaning that THC is either not present or is present in any amount less than 0.5 w/w based on the composition. In these embodiments, THC can be present in an amount less than 0.4, 0.3, 0.2, or 0.1% w/w based on the composition. In the same or other embodiments, THC can be present in an amount less than 10, 9, 8, 7, 6, 5, 4, 3, 2, or 1 ppm based on the composition.

In some embodiments, the concentration of CBD in the composition can range from about 10, 20, 30, 40, 50, 60, 70, 80, or 90 to about 350, 300, 250, 200, 150, or 100 mg/mL of the composition.

β-caryophyllene (BCP)

The compositions according to the present invention can (optionally) contain β-caryophyllene (BCP) and/or derivatives thereof as an additional active pharmaceutical agent. BCP is also named trans-(1R,9S)-8-Methylene-4,11,11-trimethylbicyclo[7.2.0]undec-4-ene or [1R-(1R,4E,9S)]-4,11,11-trimethyl-8-methylene-bicyclo[7.2.0]undec-4-ene and derivatives thereof. BCP is a natural bicyclic sesquiterpene compound found in botanical extracts of plants, including *Cannabis sativa*. It is a constituent of many essential oils, especially clove (*Syzygium aromaticum*) oil and is "generally recognized as safe" (GRAS).

It is predicted or expected that the anti-inflammatory activity of CBD will be synergistically enhanced with the addition of BCP. Caryophyllene is the only terpene known to interact with the endocannabinoid system (at CB2 receptors). β-caryophyllene selectively binds to the CB2 receptor and is a functional CB2 agonist. Furthermore, β-caryophyllene has been identified as a functional non-psychoactive CB2 receptor ligand in foodstuff and as a macrocyclic anti-inflammatory cannabinoid in cannabis. (Proc Natl Acad Sci USA. 2008 Jul. 1; 105(26):9099-104. doi: 10.1073/pnas.0803601105. Epub 2008 Jun. 23. Beta-caryophyllene is also a dietary cannabinoid).

The weight ratio of BCP and its derivatives to CBD can be from about 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, or other ratios subsumed within these ratios. The concentration of BCP in the composition can range from about 10, 20, 30, 40, 50, 60, 70, 80, or 90 to about 350, 300, 250, 200, 150, or 100 mg/mL of the composition. In one embodiment, the composition contains about 100 mg CBD and 100 mg of BCP per mL of the composition.

Commercial sources of BCP include the product shown in ANNEX A available from Sigma Aldrich (Product Number W225207: CAS Number 87-44-5). Such product contains at least 95% w/w major and minor C15H24 terpenes and up to 5% w/w impurities such as by-products of manufacturing. Thus, the BCP from Sigma Aldrich has a "purity" of at least 95%. Other embodiments of the invention can use other commercial sources of BCP having higher degrees of purity, e.g. BCP that is at least 96, 97, 98, 99, or 99.5% pure.

The BCP and derivatives thereof used in the present composition can be of synthetic or natural origin.

When used herein, a BCP "derivative" means a C15H24 minor terpene hydrocarbon and includes the minor terpenes present in the Sigma-Aldrich product.

Pharmaceutically Acceptable Solvent

Pharmaceutically acceptable solvents are employed to solubilize the active pharmaceutical agent in the present compositions. These must be suitable for parenteral administration and, preferably, via the subcutaneous (SC), intramuscular (IM), intraperitoneal (IP), and intravenous routes (IV). For lipid soluble agents such as CBD and BCP, these solvents are hydrophobic or lipophilic.

Examples of hydrophobic or lipophilic solvents include natural and synthetic solvents including medium chain (C6-C12) triglycerides (MCTs), long chain (C14-C20) triglycerides (LCTs), structured lipids, propylene glycol dicaprylate/dicaprate, vegetable oils, N-methyl-2-pyrrolidone (NMP; Pharmasolve), polyoxyethylene castor oil derivatives, dimethylacetamide (DMA), ethanol, glycerin, PEG 300, PEG 400, polyoxyethylene 20 sorbitan monooleate, propylene glycol (PG), polyglycol mono- and diesters of 12-hydroxystearic acid, solvents sold in association with the trademark Kolliphor™, and mixtures thereof.

"Medium chain triglyceride" refers to esters of glycerol having three C6 to C12 fatty acid chains, where the three fatty acid chains may be the same or different. Medium chain triglycerides are represented by the following formula:

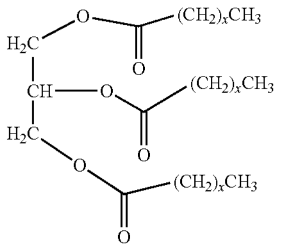

wherein each x is independently 4, 6, 8, or 10. When x is 4, the chain is referred to as a C6 fatty acid. When x is 6, the chain is referred to as a C8 fatty acid. When x is 8, the chain is referred to as a C10 fatty acid. When x is 10, the chain is referred to as a C12 fatty acid. In various embodiments, within a single molecule of triglyceride, each x is the same integer; two x are the same integer and one x is a different integer; or each x is a different integer.

Preferably, the composition contains medium chain triglycerides (MCTs) and, more preferably, those wherein C8 and C10 fatty acids make up at least 95% of the composition. The medium chain triglyceride may be synthetic or natural (e.g., produced from fractionated oils, such as coconut oil and/or palm kernel oil).

In various embodiments, the medium chain triglyceride comprises esters of (i) three C8 fatty acids; (ii) three C10 fatty acids; (iii) two C8 fatty acids and one C10 fatty acid; (iv) two C10 fatty acids and one C8 fatty acid; (v) two C8 fatty acids and one C6 fatty acid; (vi) two C10 fatty acids and one C6 fatty acid; (vii) one C8 fatty acid, one C10 fatty acid, and one C6 fatty acid; or (viii) any other combination of C6, C8, C10, and C12 fatty acids. In one embodiment, the medium chain triglyceride comprises two C8 fatty acids and one C10 fatty acid. In one embodiment, the medium chain triglyceride comprises two C10 fatty acids and one C8 fatty acid.

The skilled artisan will appreciate that a mixture of medium chain triglycerides may result from any process (e.g., fractionation, hydrogenation) used to prepare medium chain triglycerides. For example, substantially all the medium chain triglycerides obtained from fractionated coconut oil may comprise C8 and/or C10 fatty acids; however, there may be some medium chain triglycerides containing C6 and/or C12 fatty acids.

In one embodiment, the medium chain triglycerides comprise esters of (i) 0 to 2% w/w C6 fatty acid, 65 to 80% w/w C8 fatty acid, 20 to 35% w/w C10 fatty acid, and 0 to 2% w/w C12 fatty acid; (ii) 0 to 2% w/w C6 fatty acid, 50 to 65 w/w C8 fatty acid, 30 to 45% w/w C10 fatty acid, and 0 to 2% w/w C12 fatty acid; (iii) 0 to 2% w/w C6 fatty acid, 45 to 65% w/w C8 fatty acid, 30 to 45% w/w C10 fatty acid, 0 to 3% w/w C12 fatty acid; and 0 to 5% w/w linoleic acid; or (iv) 0 to 2% w/w C6 fatty acid, 45 to 55% w/w C8 fatty acid, 30 to 40% w/w C10 fatty acid, 0 to 3% w/w C12 fatty acid, and 10 to 20% w/w succinic acid. In one embodiment, the medium chain triglyceride comprises 0 to 2% w/w C6 fatty acid, 50 to 65 w/w C8 fatty acid, 30 to 45 w/w C10 fatty acid, and 0 to 2% w/w C12 fatty acid, and which is commercially available as MIGLYOL® 812 (MI Oleo GmbH, Herrengraben 31, 20459 Hamburg, Germany). The weight % is based on the total fatty acid content of the triglycerides. In one embodiment, the medium chain triglycerides may comprise up to 2% w/w C14 fatty acids.

The carrier may comprise one, two, three, four or more different medium chain triglycerides. In one embodiment, the carrier comprises a medium chain triglyceride comprising esters of two C8 fatty acids and one C10 fatty acid. In one embodiment, the carrier comprises a medium chain triglyceride comprising esters of one C8 fatty acid and two C10 fatty acids. In one embodiment, the carrier comprises two different medium chain triglycerides, where a first medium chain triglyceride comprises esters of two C8 fatty acids and one C10 fatty acid and a second medium chain triglyceride comprises esters of one C8 fatty acid and two C10 fatty acids. In one embodiment, the carrier comprises a medium chain triglyceride which comprises 0 to 2% w/w C6 fatty acid, 50 to 65% w/w C8 fatty acid, 30 to 45% w/w C10 fatty acid, 0 to 2% w/w C12 fatty acid, based on the total fatty acid content of the medium chain triglyceride.

The triglycerides may be prepared by methods known in the art and are commercially available as MIGLYOL® 810, 812, 818, 829 (IOI Oleo GmbH, Herrengraben 31, 20459 Hamburg, Germany), NEOBEE® 1053, 895, M-5 (Stepan Company, Northfield, IL), and Labrafac (Gattefosse). Vigon International, Inc. also sells MCTs containing a mixture of C8 and C10 triglycerides in a ratio (C8:C10) of from about 55:45 to about 65:35.

In another embodiment, the pharmaceutically acceptable solvent is a propylene glycol diester of saturated vegetable fatty acids with chain lengths of C8 and C10 (caprylic and capric acid). An example of one such commercially available carrier is MIGLYOL® 840 (IOI Oleo GmbH, Herrengraben 31, 20459 Hamburg, Germany).

Other pharmaceutically acceptable solvents include, without limitation, those available commercially in association with the trademarks, Solutol HS 15, Kolliphors (formerly Cremophors), Labrasol, Labrafil, and Gelucire.

Solutol HS 15 is comprised of a mixture of lipophilic and hydrophilic compounds (~70% lipophilic consisting of polyglycol mono- and diesters of 12-hydroxystearic acid and ~30% hydrophilic consisting of polyethylene glycol). Solutol HS 15 is synthesized by reacting 12-hydroxystearic acid with 15 moles of ethylene oxide.

Kolliphors™ (formerly Cremophors™) can also be used in the solvent. These are complex mixtures of various hydrophobic and hydrophilic components. Kolliphor™ EL is obtained by reacting 35 moles of ethyleneoxide with 1 mole of castor oil and comprises about 83% hydrophobic constituents of which the main component is glycerol polyethylene glycol ricinoleate. Kolliphor™ RH 40 is obtained by reacting 40 moles of ethylene oxide with 1 mole of hydrogenated castor oil and comprises about 75% hydrophobic constituents of which the main component is glycerol polyethylene glycol 12-hydroxystearate.

Labrasol is a mixture of mono-, di-, and triglycerides and mono- and di-fatty acid esters of PEG 400. Labrasol is synthesized by an alcoholysis/esterification reaction using medium-chain triglycerides from coconut oil and PEG 400, and the main fatty acid is caprylic/capric acids.

Labrafil M-1944 CS is a mixture of mono-, di-, and triglycerides and mono- and di-fatty acid esters of PEG 300. Labrafil M-1944 CS is synthesized by an alcoholysis/esterification reaction using apricot kernel oil and PEG 300, and the main fatty acid is oleic acid (58-80%).

Labrafil M-2125 CS is a mixture of mono-, di-, and triglycerides and mono- and di-fatty acid esters of PEG 300. Labrafil M-2125 CS is synthesized by an alcoholysis/esterification reaction using corn oil and PEG 300, and the main fatty acid is linoleic acid (50-65%).

Gelucire 44/14 is a mixture of mono-, di-, and triglycerides and mono- and di-fatty acid esters of PEG 1500. Gelucire 44/14 is synthesized by an alcoholysis/esterification reaction using palm kernel oil and PEG 1500, and the main fatty acid is lauric acid.

The skilled person would understand how to formulate a composition for SC, IM and IV administration based on published literature, such as Strickley, "Solubilizing Excipients in Oral and Injectable Formulations" (Pharmaceutical Research, Vol. 21, No. 2, February 2004 (© 2004), the entirety of which is incorporated herein by reference. Ingredients such as preservatives, emulsifiers, tonicity agents, salts, buffering agents, diluents, may also be used.

In preferred embodiments, the composition comprises an effective amount of CBD, or an effective amount of each of CBD and BCP, dissolved in MCTs, wherein the composition is substantially free of water and micelles.

Methods of Administration

The present compositions are for parenteral administration, e.g. via intravenous (IV), subcutaneous (SC), intraperitoneal (IP), and intramuscular (IM) injection. The following examples show that the present compositions can be useful in reducing leukocyte mediated inflammation, cardiac fibrosis and/or cardiac hypertrophy.

The present compositions can be administered at least once weekly, or at least once every 6, 5, 4, 3, or 2 days. The composition can also be administered at least once daily, or at least twice daily. For each administration, at least about 0.1, 1, 2, 3, 4, 5, 6, 7, 8, 9, 10, 15, or 20 mg of the pharmaceutically active agent is administered per kg body weight. The treatment period can be for 6, 5, 4, 3, or 2 months, or for 8, 7, 6, 5, or 4 weeks. In the case of chronic conditions (e.g. heart failure), it is envisioned that a very low dose can be administered for an indefinite period, the dose being selected to avoid long term toxicity. In one embodiment, 1 mg/kg body weight can be administered at least once a week, or at least once every 1, 2, 3, 4, or 5 days, for an indefinite period.

EXAMPLES

Example 1—CBD Decreases Angiotensin II-Mediated Hypertrophy in H9c2 Cells In Vitro A study was conducted to determine the effect of CBD in a model of cardiomyocyte hypertrophy, using H9c2 cells, a cardiomyocyte cell line, in vitro. In this study, H9c2 cells grown in a culture medium were divided into four groups. To one group nothing was added ("Control"). To the second, third and fourth groups, Angiotensin II was added to the culture medium ("Ang") to give a final concentration of 1.0 μM. The Angiotensin II was added to induce hypertrophy. To the third group, CBD was also added to give a concentration of 0.1 μM ("Ang+CBD 0.1 μM"). Finally, to the fourth group, CBD was also added to give a concentration of 1 μM ("Ang+CBD 1 μM").

Figure 2:
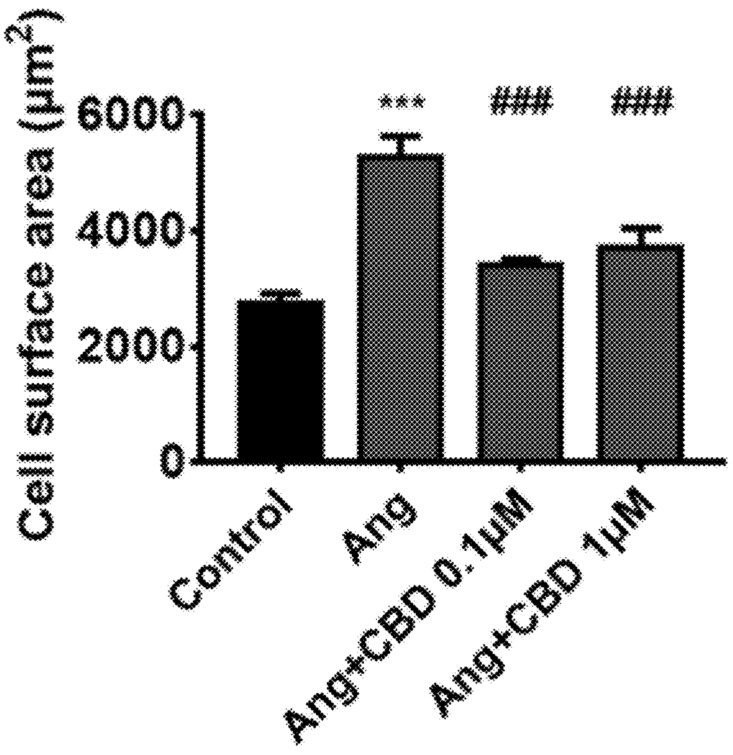
FIG. 2 is a graph showing the effect of administration of CBD at different doses on the cell surface area of H9c2 cells, in the in vitro model of cardiomyocyte hypertrophy.

FIG. 1 contains representative confocal microscopy images of the H9c2 cells in each group. The images were obtained using a model with the same parameters and cell staining, to determine the surface area per cell, was achieved using calcein fluorescent dye. As can be seen in this figure, the cells of the second group had a cell surface area that was significantly larger than the cell surface area of the cells in the first group. The cells of the $3^{rd}$ and fourth groups had cell surface areas that were significantly smaller than that of the second group. The results are summarized in FIG. 2, wherein each group comprises at least 3 independent replicates per group.

Thus, the study demonstrated that CBD exerts an effect on cardiac cells and is effective to reduce the degree of hypertrophy caused by Angiotensin II administration to H9c2 cells in vitro.

The study was repeated using H9c2 cells grown in a culture medium divided into seven groups. To one group nothing was added ("CTRL"). To the second, fourth, fifth, sixth, and seventh groups, Angiotensin II was added to the culture medium ("ANG") to give a final concentration of 1.0 μM. The Angiotensin II was added to induce hypertrophy. To the third group, CBD was added to give a concentration of 0.1 μM ("CBD 0.1 μM") as an additional control group. CBD was also added to (a) the fourth group to give a concentration of 0.001 μM ("ANG+CBD 0.001 μM"), (b) the fifth group to give a concentration of 0.01 μM ("ANG+CBD 0.01 μM"), (c) the sixth group to give a concentration of 0.1 μM ("ANG+CBD 0.1 μM"), and, finally, (d) the seventh group to give a concentration of 1 μM ("ANG+CBD 1 μM").

Figure 3A:
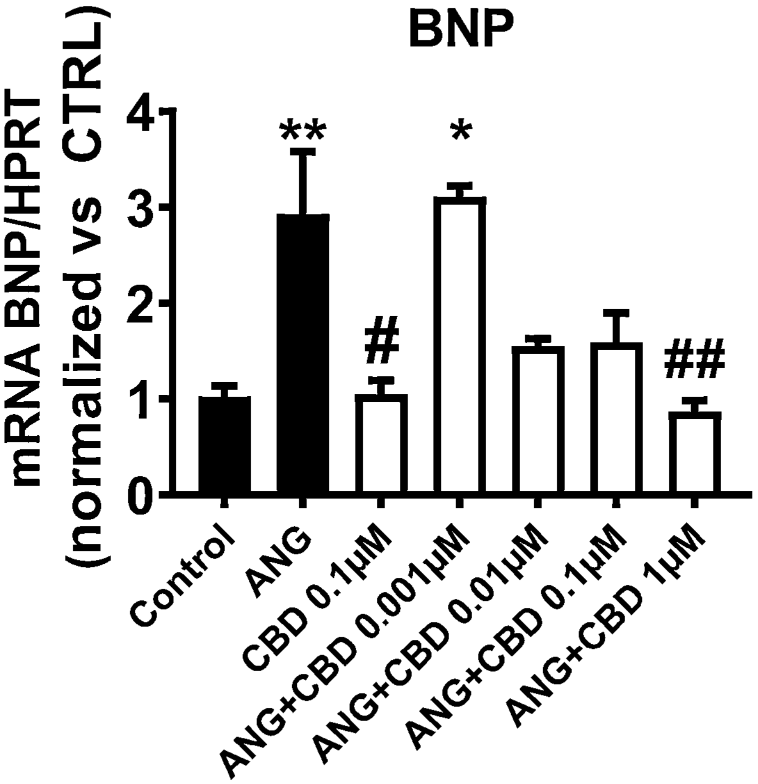
FIGS. 3*a* and 3*b* are graphs showing the reduction in the level of mRNA expression of B-type natriuretic peptide (BNP) (a remodeling biomarker), and collagen, respectively, by CBD administered at different doses in the in vitro model of cardiomyocyte hypertrophy.
Figure 3B:
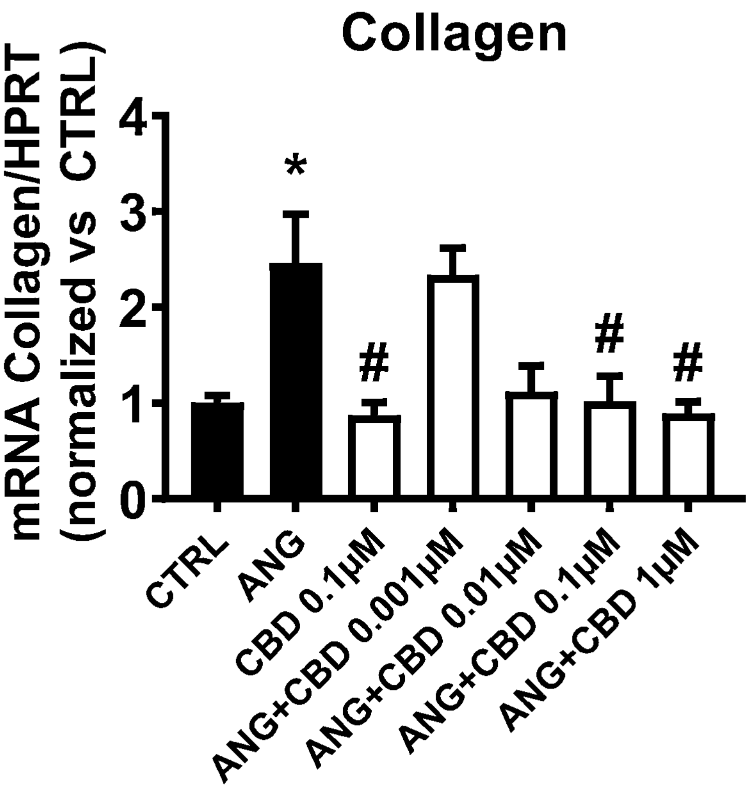
Figure 4:
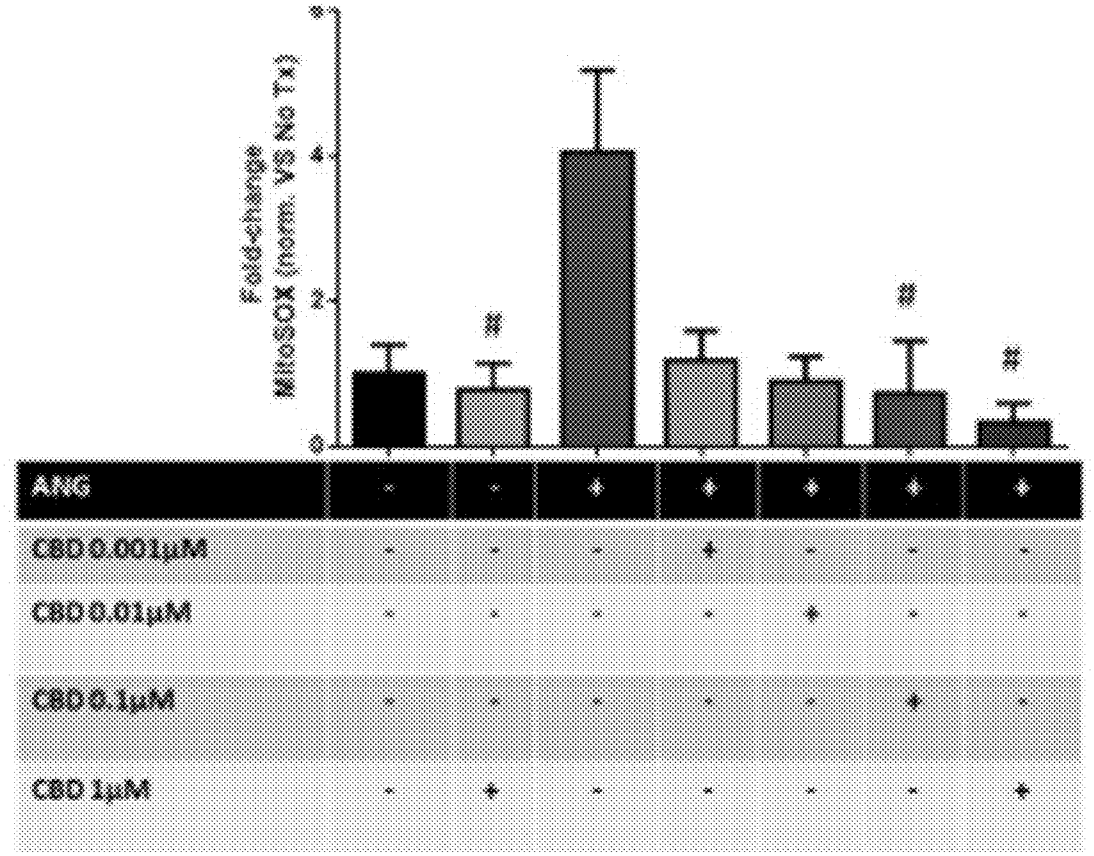
FIG. 4 is a graph showing the reduction of mitochondrial reactive oxygen species (MitoSOX), a marker for inflammation, by CBD administered at different doses in the in vitro model of cardiomyocyte hypertrophy.

In these H9c2 cell groups, there was a dose-dependent reduction of the mRNA level of expression of BNP (a heart remodeling biomarker) (see FIG. 3*a*) and collagen (see FIG. 3*b*). BNP was significantly reduced in the ANG+CBD 1 μM group compared to the ANG group (FIG. 3*a*), and collagen was significantly reduced in the angiotensin-treated CBD groups at 0.1 and 1 μM concentrations compared to the ANG group (FIG. 3*b*). Mitochondrial reactive oxygen species (ROS), a marker for inflammation, were also reduced down to control levels (see FIG. 4).

These experiments demonstrate that CBD exerts an anti-hypertrophic effect on cardiac cells, which is reflected at the molecular level by markedly reducing remodeling biomarkers and mitochondrial ROS, a mediator of inflammation.

Figure 5:
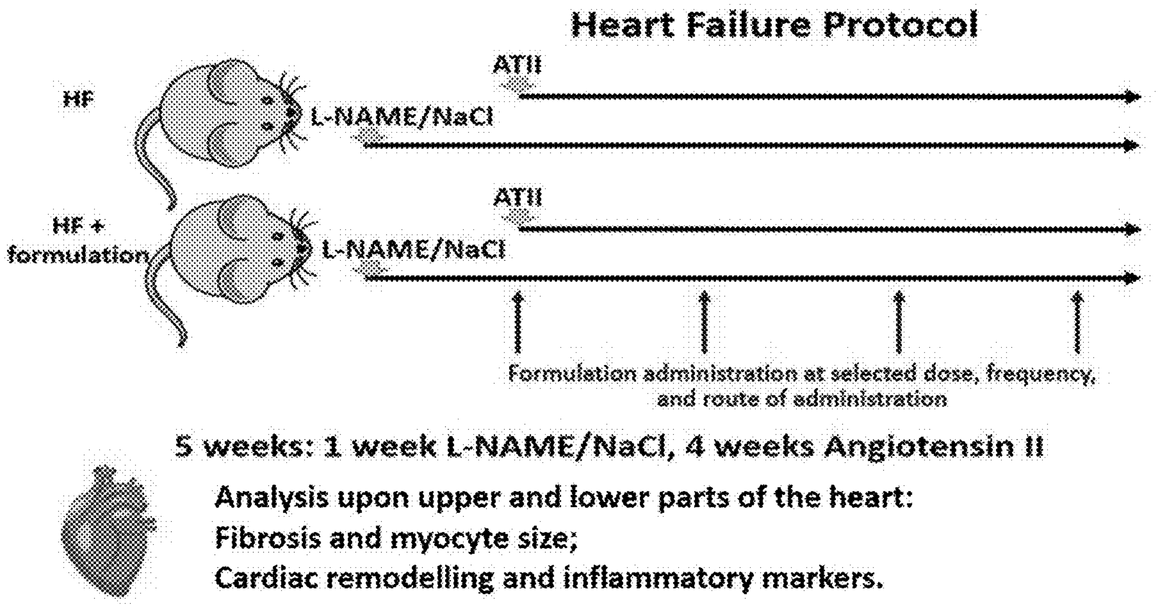
FIG. 5 depicts a representation of the experimental design that was used to determine the effect of administering CBD in a murine model of non-ischemic heart failure.
Figure 6A:
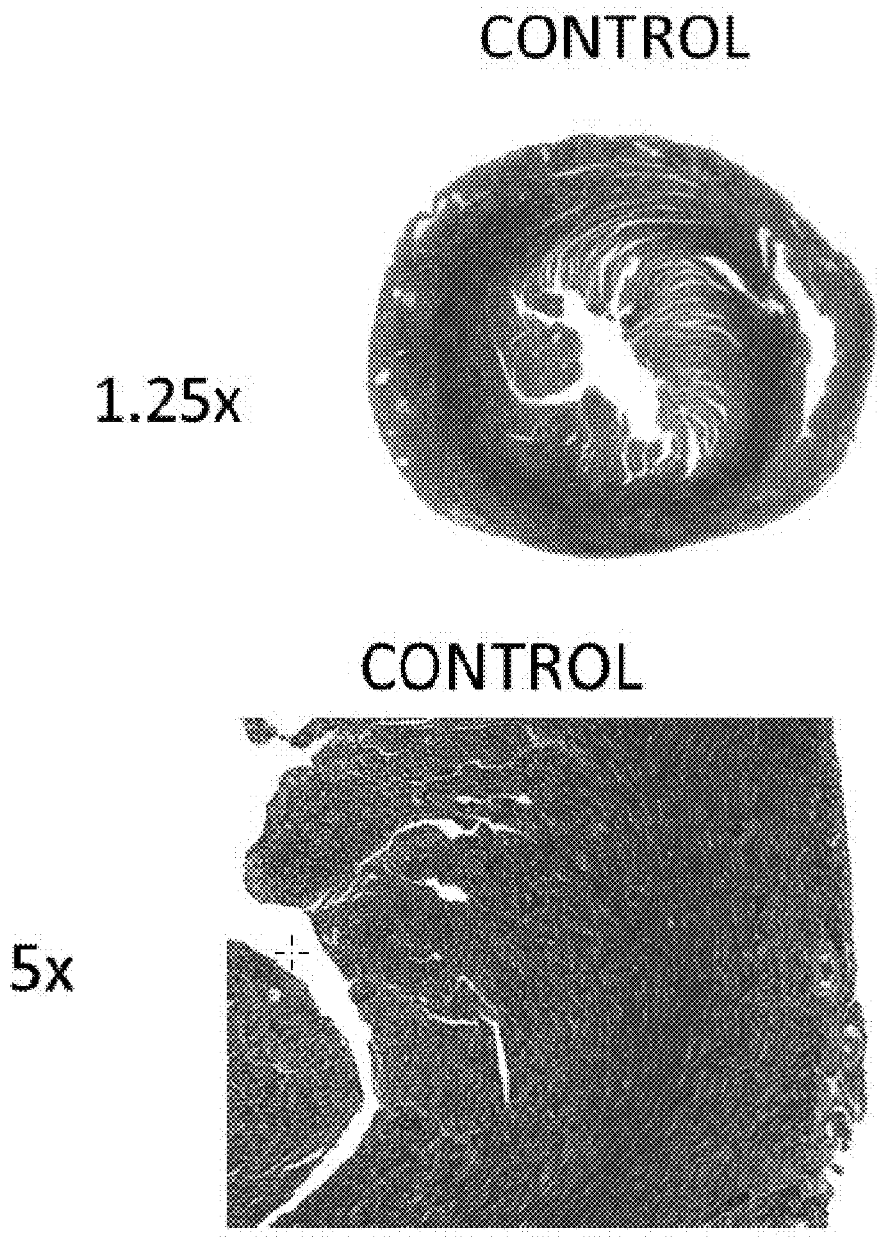
FIGS. 6A-6D show representative slides of murine heart tissue stained with Masson's trichrome, which show a reduction in fibrosis (reduction in the blue stain) following administration of CBD in the experiment of FIG. 5.
Figure 6B:
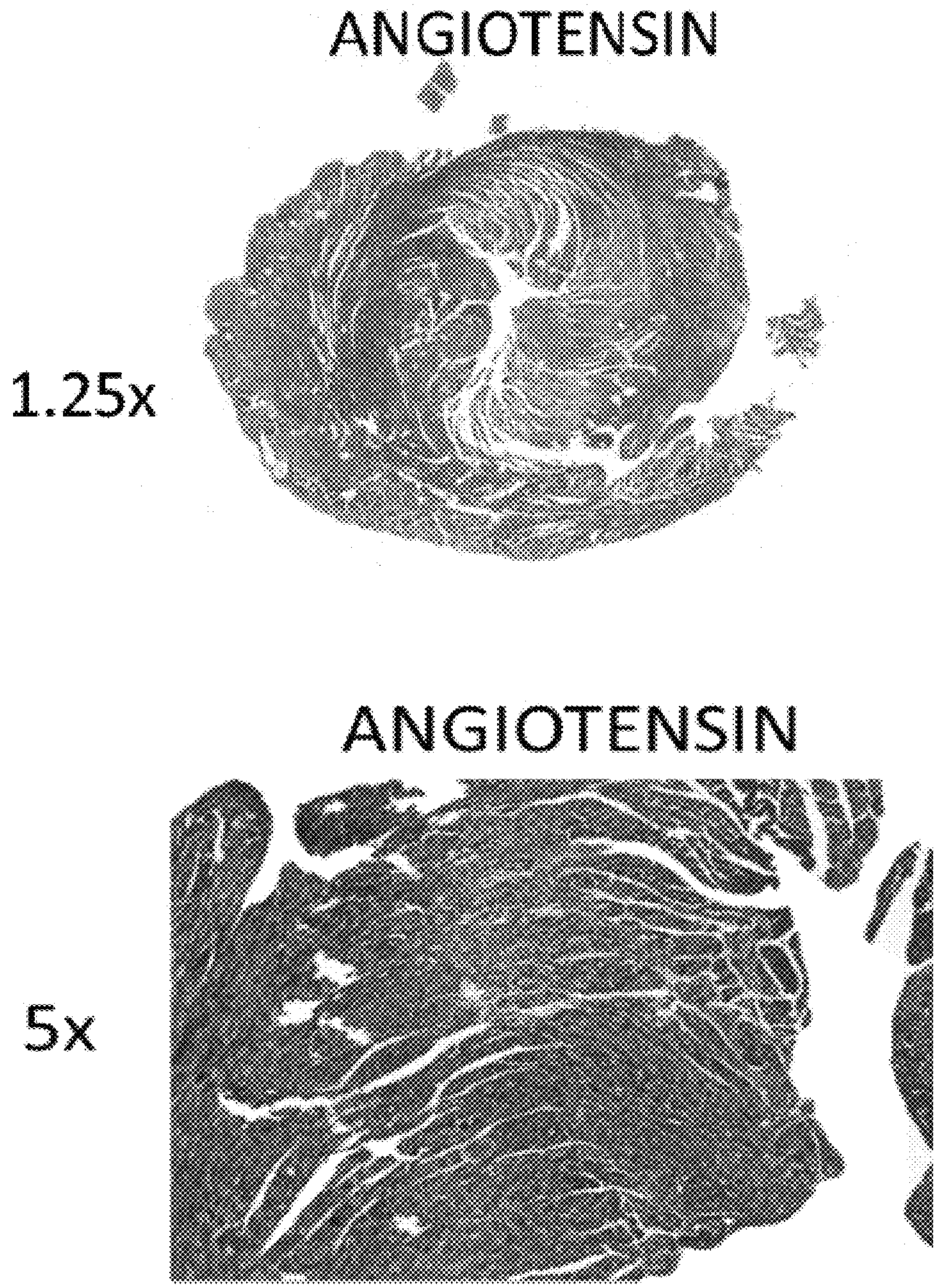
Figure 6C:
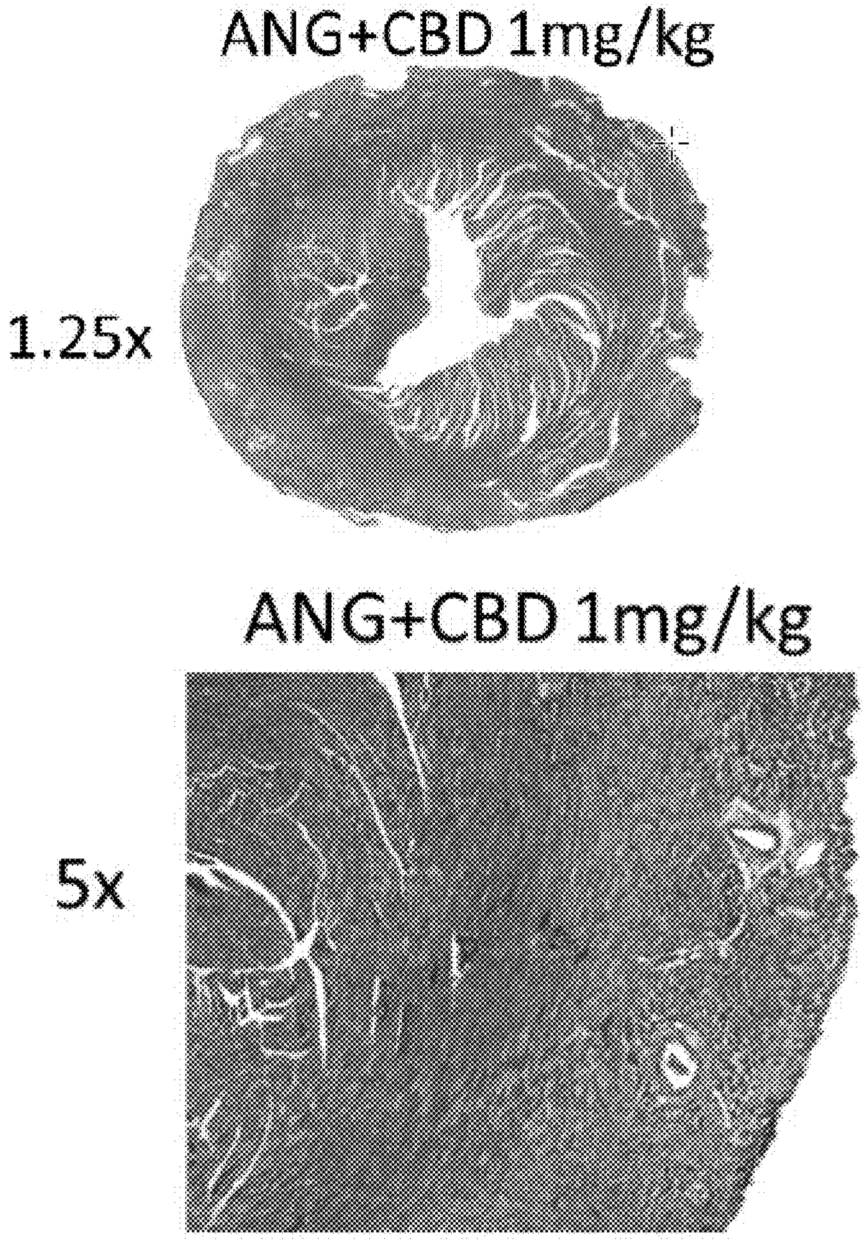
Figure 6D:
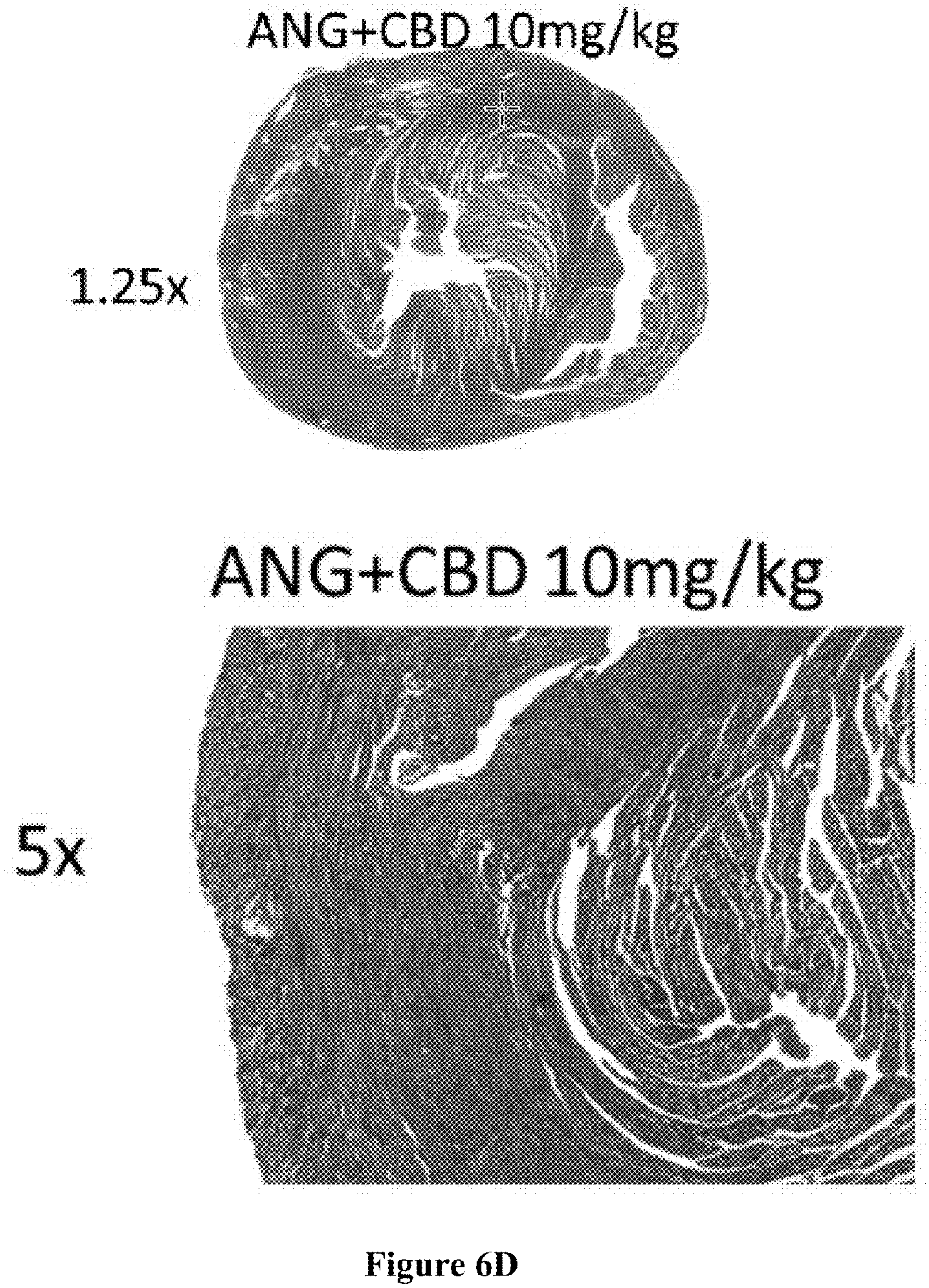

Example 2—CBD Decreases Fibrosis, Myocyte Area, Remodelling Parameters, and Pro-Inflammatory Cytokines, as well as Increases Anti-Inflammatory Cytokine, in a Murine Model of Cardiac Inflammation and Heart Failure Tests were done to evaluate the potential for CBD in treating or preventing heart failure in a mouse model of non-ischemic heart failure (HF) illustrated in FIG. 5.

Three to four week old male C57BL/6 laboratory mice were used in the experiments. The mice were divided into four groups. A first group (the Control) received nothing. The second group of mice (Angiotensin) was provided with water containing 0.1 mg/ml of N(gamma)-nitro-L-arginine methyl ester (L-NAME) and 1% sodium chloride (NaCl) ad libitum for one week. Following this, 0.7 mg/kg/week of Angiotensin II was administered subcutaneously for 4 weeks using osmotic pumps. The third group and fourth group were subjected to the same protocol as the second group, however, the third group (ANG+CBD 1 mg/kg) and fourth group (ANG+CBD 10 mg/kg) also received synthetic CBD subcutaneously in an amount of 1 mg/kg and 10 mg/kg, respectively, once every 3 days during the same four week period. The CBD compositions used in this experiment consisted of CBD dissolved in PEG400.

After four weeks of treatment, cardiac tissue was evaluated for fibrosis and myocyte hypertrophy and changes in remodeling and inflammation biomarkers.

Figure 7:
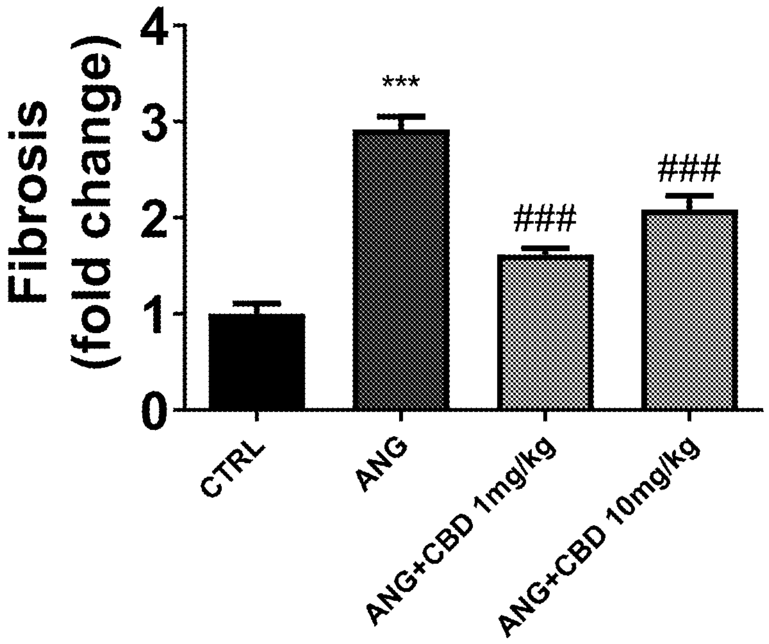
FIG. 7 is a graph showing the reduction in fibrosis following CBD administration in the experiment of FIG. 5.
Figure 8:
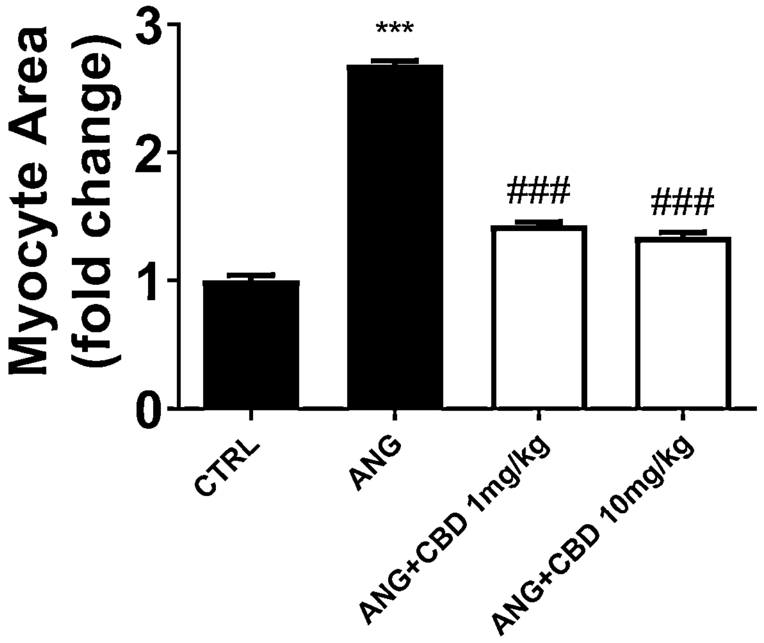
FIG. 8 is a graph showing a reduction in myocyte area (hypertrophy) following CBD administration in the experiment of FIG. 5.

A number of changes, including increased fibrosis and increased myocyte area (hypertrophy), were observed in the hearts of the mice in the second, third and fourth groups, compared to the first group. FIGS. 6A, 6B, 6C, and 6D show representative slides of heart tissue taken from each of the four groups. The heart tissue was stained with Masson's Trichrome to show an increased level of fibrotic tissue (as evidenced by the blue staining) in the mice of the $2^{nd}$, $3^{rd}$, and $4^{th}$ groups relative to the $1^{st}$ group (the Control), and a decreased level of fibrosis in the mice in the third and fourth groups relative to the second group. This information is depicted graphically in FIG. 7. The myocyte area was also measured in all four groups and the results are also shown in FIG. 8. FIGS. 7 and 8 show that CBD at both 1 mg/kg and 10 mg/kg were effective to reduce cardiac fibrosis and myocyte area in a murine model of heart failure. Each group comprised at least three independent replicates per group.

Figure 9:
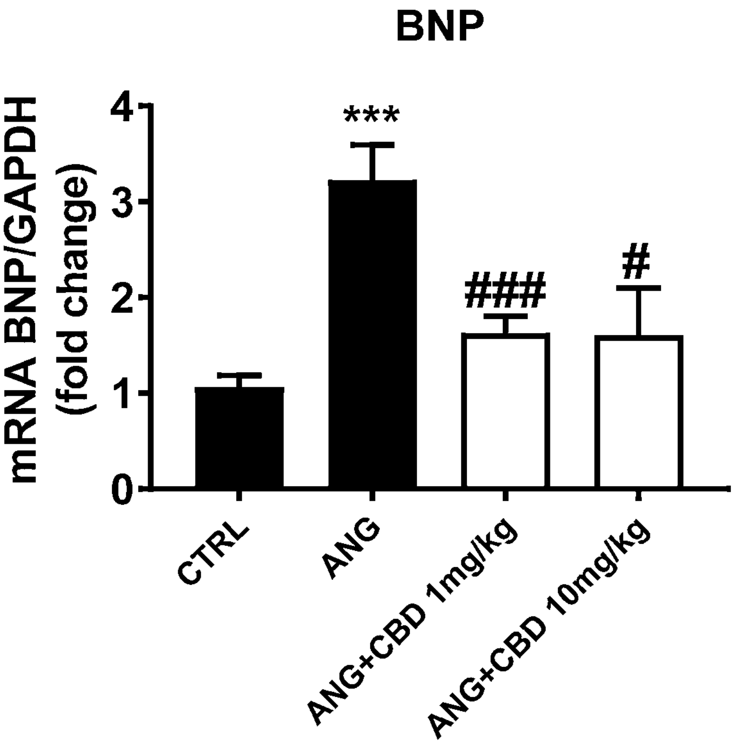
FIG. 9 is a graph showing a reduction in the level of mRNA expression of BNP following CBD administration in the experiment of FIG. 5.

FIG. 9 shows the level of mRNA expression of b-type natriuretic peptide (BNP) in the heart tissue of the mice in all four groups, measured by qPCR. Both 1 and 10 mg/kg CBD groups show a significant reduction in BNP expression in the heart compared with the ANG group. Each group comprised at least three independent replicates per group. BNP is a remodeling marker and a clinical marker of myocardial stretch (pressure overload) which is positively associated with cardiac dysfunction and heart failure (see, e.g., Glezeva et al.). There is clinical evidence that, in patients with chronic heart failure (CHF), reducing the BNP level to <100 pg/mL reduced the risk of CHF-related death or hospital stays (Jourdain et al., Plasma brain natriuretic peptide-guided therapy to improve outcome in heart failure: the STARS-BNP Multicenter Study, J Am Coll Cardiol. 2007 Apr. 24; 49(16): 1733-9). Thus, this reduction in BNP may also show that CBD can prove beneficial in the treatment and/or prevention of heart failure.

Figure 10A:
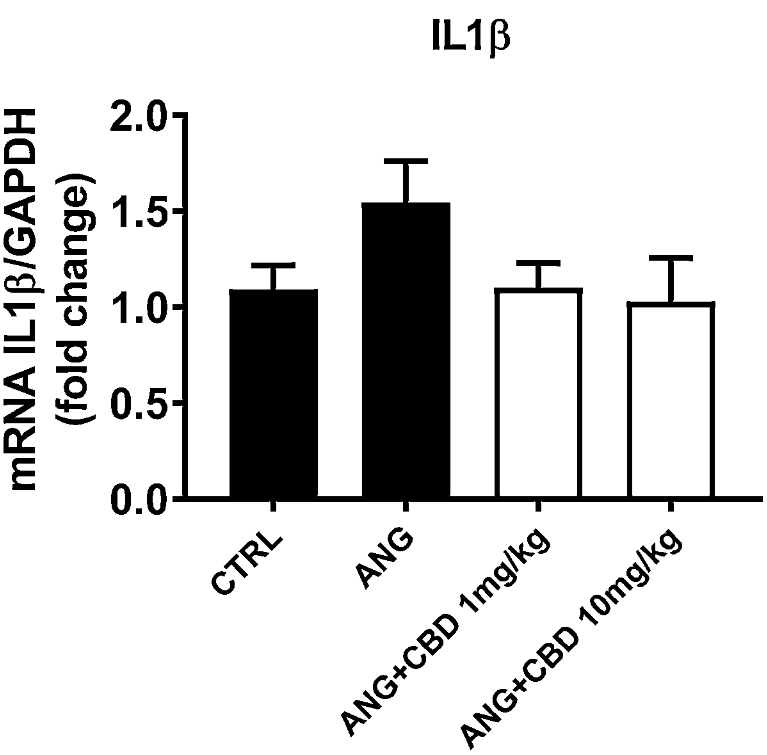
FIGS. 10*a*, 10*b*, and 10*c* are graphs showing the level of mRNA expression of pro-inflammatory cytokines IL1β and IL6 and the anti-inflammatory cytokine IL10, respectively, following CBD administration in the experiment of FIG. 5.
Figure 10B:
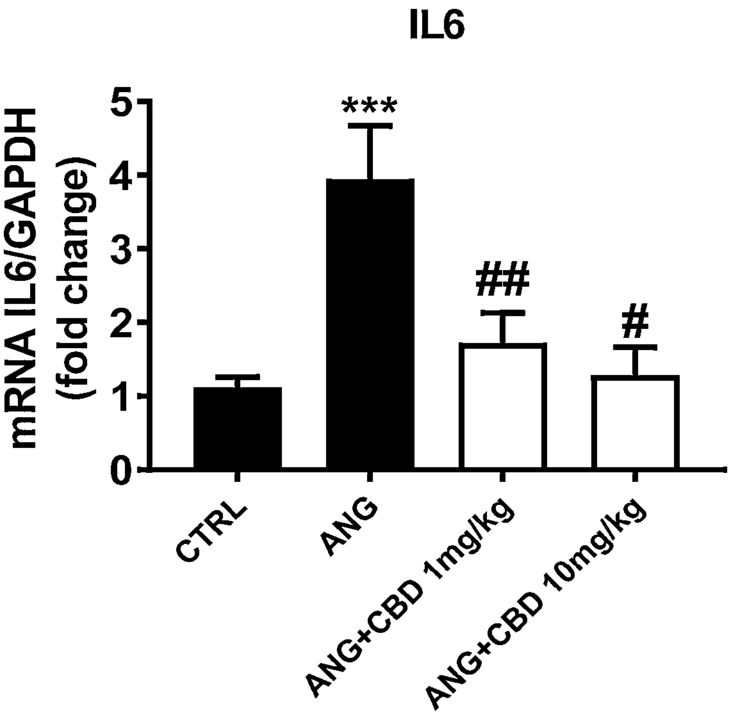
Figure 10C:
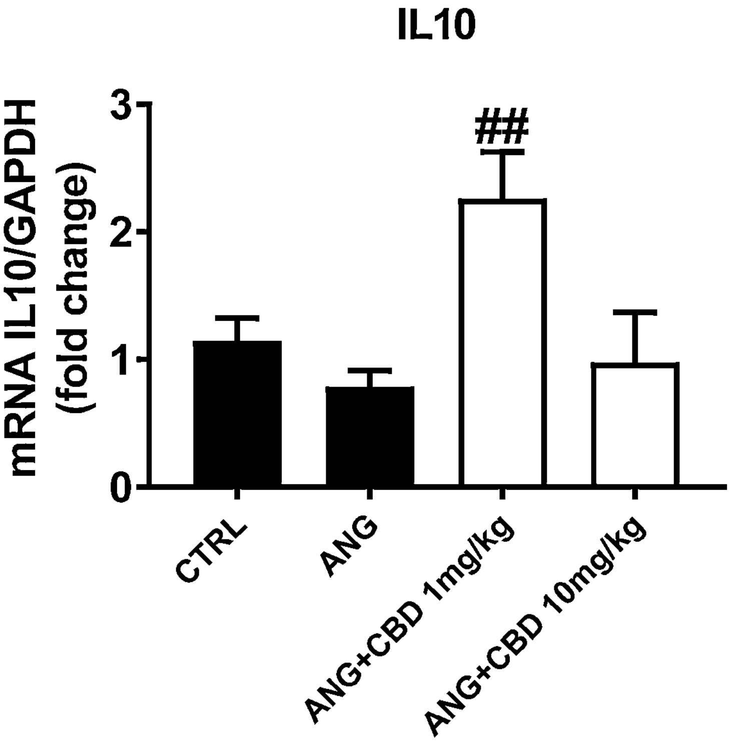

Additionally, mRNA expression of the pro-inflammatory cytokine IL1β showed a trend to be reduced to control levels (FIG. 10*a*), with mRNA expression of the pro-inflammatory cytokine IL6 significantly decreased for both 1 and 10 mg/kg body weight doses of CBD (FIG. 10*b*). mRNA expression of IL10 was significantly increased for the 1 mg/kg body weight dose of CBD (FIG. 10*c*). Each group comprised at least three independent replicates per group. IL10 is an anti-inflammatory cytokine also known as human cytokine inhibitory factor that is capable of inhibiting synthesis of pro-inflammatory cytokines. There is evidence to suggest IL-10 has a role in vascular protection; in an animal model, a lack of IL-10 was shown to be responsible for COX-2/thromboxane A2-dependent vascular endothelial and cardiac dysfunction (Gautam Sikka et al., Interleukin 10 Knockout Frail Mice Develop Cardiac and Vascular Dysfunction with Increased Age, Experimental Gerontology, vol. 48, Issue No. 2, Feb. 2013, pp. 128-135).

In summary, the inventors observed a dose-dependent reduction of remodeling and inflammation parameters resulting from the administration of CBD in the mouse model of non-ischemic HF. Regarding remodeling, significant reductions were observed for fibrosis, myocyte hypertrophy, as well as gene expression of BNP. Inflammation parameters were improved, namely, the levels of pro-inflammatory cytokines IL1β and IL6 were reduced, and the level of anti-inflammatory cytokine IL10 was significantly increased, with CBD administration. These findings support the beneficial role of CBD in treating or preventing heart failure and other conditions such as acute myocarditis, inflammatory cardiomyopathy, cardiac sarcoidosis, acute pericarditis, myocardial damage resulting from the administration of certain anti-cancer drugs and possibly the development or progression of coronary atherosclerotic lesions by reducing cardiac inflammation, and associated hypertrophy, and fibrosis.

Example 3—CBD Reduces Activation of Human Lymphocytes and Monocytes

A further study was performed to determine the effect of CBD on the expression of CD69 (a marker of leukocyte activation) by human lymphocytes and monocytes that had been activated by ionomycin (1 μg/mL) and phorbol myristate acetate (PMA, 50 ng/mL) in vitro.

Mononuclear cells from a healthy human donor were isolated using a gradient method with Ficoll-Pacque™ Healthcare. Cells were washed with RPMI media with 10% FCS and 1% Penn/Strept and then placed in 12 well trays at $1\times10^6$ cells/mL and stimulated for 4 hours with Ionomycin 1 μg/ml and 50 ng/ml PMA. CBD was added 15 minutes before using DMSO as a vehicle. After the stimulation, cells were washed again and resuspended in 150 μL staining buffer (PBS+1% BSA). An optimized protocol for surface marker staining was used. CD69 was added to the cells, which were then incubated for 15 minutes in the dark at room temperature. After this, cells were washed twice with PBS+1% BSA and resuspended in 150 μL buffer. Cells were kept at 4 degrees prior to being analyzed in a FACSCanto™ II cytometer. Cell populations were determined by FSC/SSC. The number of events were at least 2000 events per gate. Data was saved as FCS 3.0 files. The data was analyzed with FlowJo X. Doublets were discriminated with an exclusion gate of FSC-A/FSC-W. Gating for lymphocytes and monocytes was determined by FSC-A/SSC-A. The frequency and expression of CD69-FITC was analyzed in its FITC channel.

Figure 11:
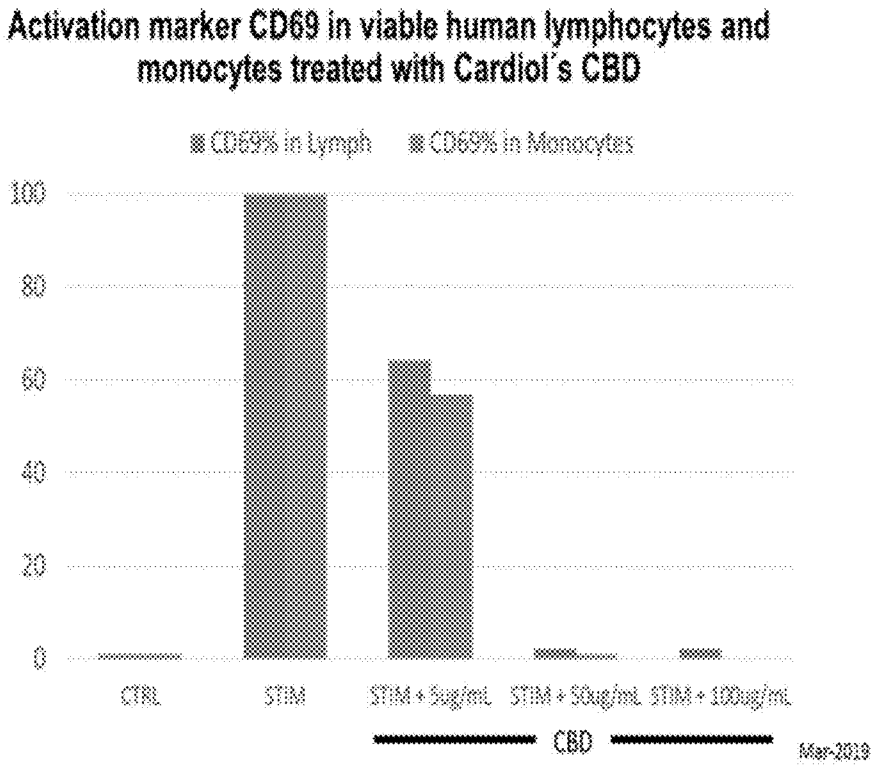
FIG. 11 is a graph showing the effect of CBD administration on the expression of CD69 by stimulated/activated monocytes and lymphocytes (white blood cells) in a separate experiment.

FIG. 11 shows that the administration of CBD in an amount of 5 μg/mL or greater (per mL of cell culture fluid containing RPMI with 10% fetal calf serum and 1% penicillin/streptomycin) reduced the level of expression of CD69 by both monocytes and lymphocytes. Thus, this experiment shows that CBD can reduce leukocyte activation in vitro and can be expected to reduce inflammation, one of the underlying pathologies of heart failure.

INDUSTRIAL APPLICABILITY

The experiments described herein show CBD to be useful in treating or preventing a heart condition selected from the group consisting of heart failure (e.g. HFpEF), acute myocarditis, toxicity caused by anti-cancer therapies (e.g. doxorubicin, checkpoint inhibitors), acute pericarditis, cardiac sarcoidosis, inflammatory cardiomyopathy, and atherosclerosis, by reducing cardiac inflammation, and associated hypertrophy, and fibrosis.

Acute inflammation is a protective response of the body's immune system to danger signals, including infections and damaged cells, to eliminate infection and repair damaged tissues. Inflammation leads to increased blood flow and permeability of blood vessels so that immune cells can access the site of infection or damage. Following tissue repair and elimination of the danger signal, it is vital that the initial inflammatory and reparative response be switched off. This is usually a result of the accumulated inflammatory cells undergoing cell death by apoptosis and their uptake by macrophages via efferocytosis, a process which induces an anti-inflammatory response, terminating the inflammation. A failure of this off switch results in ongoing chronic inflammation, which is seen in many disorders including heart failure.

As mentioned above, factors predisposing people to heart failure include ageing, diabetes, obesity, and hypertension. These conditions are associated with an increase in low grade background inflammation. Without being bound by theory, it is believed that chronic inflammation results from, amongst other things, a failure of efferocytosis of apoptotic cells and causes an increase in cell death of cardiomyocytes (heart muscle cells), increased fibrogenesis (the laying down of scar tissue), and reduced heart function due to the weakening and stiffening of the heart muscle resulting from these mechanisms.

Acute myocarditis is the leading cause of sudden cardiac death in people under 35. It is characterized by inflammation in the heart muscle (myocardium). It has many causes, but the most common is a viral infection. In most patients the immune system is effective in clearing the virus in five to seven days, inflammation subsides, and the individual makes a full recovery. In a proportion of patients, however, the inflammation in the heart persists—perhaps as an autoimmune process—and causes decreased heart function with symptoms and signs of heart failure. In some cases, this becomes progressive and leads to a chronic dilated cardiomyopathy which is the most common reason for heart transplantation.

The embodiments described above are by way of example only and are not intended to limit the scope of the invention as described fully herein and defined by the following claims.

The invention claimed is:

1. A method of treating or preventing a heart condition selected from the group consisting of heart failure, myocarditis, toxicity caused by anti-cancer therapies, acute pericarditis, cardiac sarcoidosis, inflammatory cardiomyopathy, and atherosclerosis in a subject in need thereof, the method comprising administering an effective amount of cannabidiol (CBD) to the subject, wherein the administration of the CBD effects (i) a reduction of a level of B-type natriuretic peptide (BNP), (ii) a reduction of a level of cluster of differentiation 69 (CD69), (iii) an increase in a level of cytokine interleukin 10 (IL10), or (iv) a combination of any of (i) to (iii) in the subject.

2. The method of claim 1, wherein the administration of the CBD effects at least 2 of (i) to (iii).

3. The method of claim 2, wherein the administration of the CBD effects all of (i) to (iii).

4. The method of claim 1, wherein the heart failure is heart failure with preserved ejection fraction (HFpEF).

5. The method of claim 1, wherein the myocarditis is acute myocarditis.

6. The method of claim 1, wherein the CBD is administered at least once weekly.

7. The method of claim 6, wherein the CBD is administered at least 2 or 3 times weekly.

8. The method of claim 7, wherein the CBD is administered at least once daily.

9. The method of claim 8, wherein the CBD is administered at least twice daily.

10. The method of claim 6, wherein each administration consists of administering from about 1 mg to about 20 mg of the CBD per kg body weight.

11. The method of claim 1, wherein the CBD is in a parenteral composition, the parenteral composition further comprising an effective amount of at least one solvent for solubilizing the CBD in the composition.

12. The method of claim 11, wherein the parenteral composition is adapted for subcutaneous or intramuscular administration.

13. The method of claim 11, wherein the composition is free of micelles.

14. The method of claim 11, wherein the composition is substantially free of water.

15. The method of claim 11, wherein the composition further comprises an effective amount of at least one additional pharmaceutically active agent.

16. The method of claim 15, wherein the at least one additional pharmaceutically active agent is beta-caryophyllene.

17. The method of claim 11, wherein the solvent is selected from the group consisting of natural and synthetic medium chain (C6-C12) triglycerides (MCTs).

18. The method of claim 17, wherein at least about 95% of the MCTs consists of a C8 triglyceride, a C10 triglyceride, or a mixture thereof.

19. The method of claim 11, wherein the CBD is present in an amount up to about 350 mg/mL of the composition.

20. The method of claim 11, wherein the CBD is present in an amount from about 10 mg/mL of the composition.

* * * * *